United States Patent
Booth

(10) Patent No.: US 6,902,531 B2
(45) Date of Patent: Jun. 7, 2005

(54) PNEUMATIC CONTROL OF BLOOD PRESSURE DETERMINATIONS

(75) Inventor: John W. Booth, Tampa, FL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 123 days.

(21) Appl. No.: 10/427,827

(22) Filed: May 1, 2003

(65) Prior Publication Data

US 2004/0220482 A1 Nov. 4, 2004

(51) Int. Cl.$^7$ .................................................. A61B 5/02
(52) U.S. Cl. ........................................................ 600/490
(58) Field of Search .............................. 600/490–499, 600/481, 485

(56) References Cited

U.S. PATENT DOCUMENTS

| | | | | |
|---|---|---|---|---|
| 4,475,554 A | * | 10/1984 | Hyndman | 600/473 |
| 4,501,280 A | * | 2/1985 | Hood, Jr. | 600/490 |
| 4,872,461 A | * | 10/1989 | Miyawaki | 600/494 |
| 4,938,227 A | * | 7/1990 | Niwa et al. | 600/495 |
| 6,283,922 B1 | * | 9/2001 | Goto et al. | 600/485 |
| 6,478,745 B2 | * | 11/2002 | Nakagawa et al. | 600/499 |

OTHER PUBLICATIONS

Disclosure Document, 3 pages date stamped by the USPTO on May 5, 1994, and 1 page dated Jul. 12, 1994.

* cited by examiner

Primary Examiner—Robert S. Nasser
Assistant Examiner—Navin Natnithithadha
(74) Attorney, Agent, or Firm—Andrus, Sceales, Starke & Sawall, LLP

(57) ABSTRACT

A method and apparatus for pneumatic control of a blood pressure determination are disclosed. The method and apparatus comprise an inflatable cuff for obtaining a blood pressure measurement from a patient, a hose configured to operate with a pressurizing apparatus for providing pressurization of the inflatable cuff, the hose including a patient end and a non-patient end. In addition the method and apparatus comprise a pneumatic switch coupled to the inflatable cuff near the patient end of the hose.

29 Claims, 9 Drawing Sheets

PNEUMATIC CONTROL OF BLOOD PRESSURE DETERMINATIONS

BACKGROUND OF THE INVENTION

The field of the invention is patient monitoring systems. More particularly, the invention relates to a method and apparatus for regulating a blood pressure determination from the patient end of a patient monitoring system.

The heart muscles of humans periodically contract to force blood through the arteries. As a result of this pumping action, pressure signals exist in these arteries and cause them to cyclically change volume. The baseline pressure for these signals is known as the diastolic pressure and the peak pressure for these signals is known as the systolic pressure. A further pressure value, known as the "mean arterial pressure" (MAP), represents a time-weighted average of the blood pressure. The systolic, MAP and diastolic values for a patient are useful in monitoring the cardiovascular state of the patient, in diagnosis of a wide variety of pathological conditions, and in treating disease. Therefore, it is a great advantage to a clinician to have an automatic blood pressure monitor which can accurately, quickly, and non-invasively estimate these blood pressure values.

In many instances, a clinician will use a long tube or hose connected to an automatic blood pressure monitor when measuring a patient's blood pressure. This is often necessary when the monitor is wall mounted or there is no room to locate the device next to the patient. In these types of situations, the clinician must apply the cuff to the patient and then move some distance away from the patient to activate the blood pressure determination process. This can be time consuming and inefficient since it is typically advantageous to remain near a patient to check other vital signs or offer more personal care for the patient. Thus, there exists a need for a method and apparatus for controlling a blood pressure determination from the patient end of the tube or hose, thereby allowing the clinician to remain next to the patient during the automated determination.

SUMMARY OF THE INVENTION

One embodiment of the present invention provides an apparatus for pneumatic control of a blood pressure determination, the apparatus including an inflatable cuff for obtaining a blood pressure measurement from a patient, a hose configured to operate with a pressurizing apparatus for providing pressurization of the inflatable cuff, the hose comprising a patient end and a non-patient end, and a pneumatic switch coupled to the inflatable cuff near the patient end of the hose.

Another embodiment of the present invention provides a system for pneumatically controlling a blood pressure determination, the system including means for acquiring a blood pressure measurement from a patient, means for pneumatically isolating a lumen and creating a pressure signal therein, means for sensing a pressure signal, and means for providing a signal based on the pressure signal to a microprocessor in order to control overall operation of the system.

Another embodiment of the present invention provides a method of pneumatically controlling a blood pressure determination, the method comprising pressurizing an inflatable cuff of a blood pressure measurement device in order to obtain a blood pressure determination. In addition, the method includes depressing a pneumatic switch coupling the inflatable cuff to at least one lumen near a patient end of the lumen, whereby depressing the controller switch pneumatically isolates the lumen and creates a pressure signal therein. Further, the method includes using a sensor to sense the pressure signal and signaling a microprocessor as a result of the pressure signal in order to control the blood pressure determination.

Another embodiment of the present invention provides a method of pneumatically controlling a transfer of medical data, the method including acquiring medical data from a patient using medical apparatus, controlling the acquisition of medical data by using a switch configured to pneumatically create a pressure change in the medical apparatus that may be sensed by a sensor. In addition, the method includes signaling a microprocessor of the change, wherein the microprocessor toggles the acquisition of the medical data based on preprogrammed logic.

Another embodiment of the present invention provides a computer program product for controlling a blood pressure determination based on a pneumatic controller switch, the computer program product comprising a means for acquiring a blood pressure measurement from a patient, a means for pneumatically isolating a lumen and creating a pressure signal therein, a means for sensing the pressure signal, and a means for providing a signal based on the pressure signal to a computer useable medium having computer logic for enabling at least one processor in a computer system to toggle control of the blood pressure determination.

DESCRIPTION OF THE PREFERRED EMBODIMENT

Figure 1A:
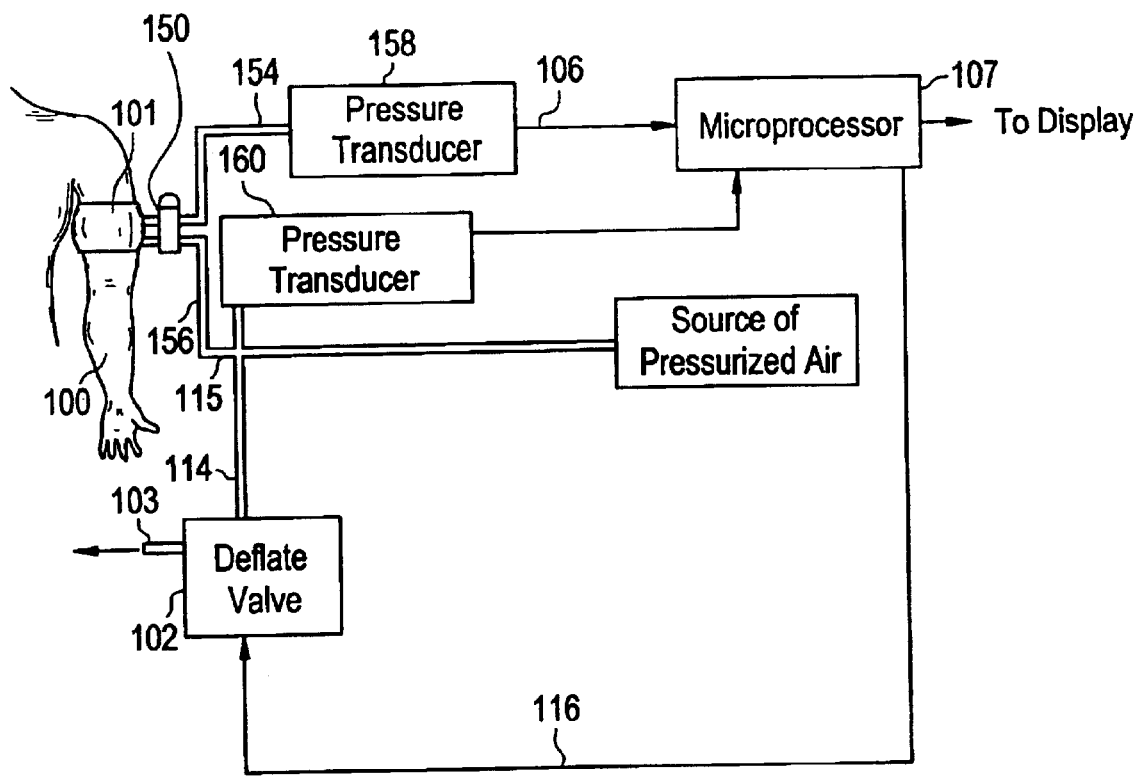
FIG. 1A is a diagram of a non-invasive blood pressure monitoring system in accordance with an embodiment of the present invention.

FIG. 1A shows a blood pressure determination system including the arm of a human subject wearing a flexible inflatable cuff 101 capable of occluding the brachial artery when fully inflated. As cuff 101 is deflated using deflate valve 102 having exhaust 103, the arterial occlusion is gradually relieved. The deflation of cuff 101 via deflate valve 102 is controlled by microprocessor 107 via control line 116.

Referring to FIG. 1A, a pressure transducer 158 is coupled by a hose (e.g. tube, duct, etc.) 154 to the cuff 101 for sensing the pressure therein. Cuff pressure levels in the artery are sensed by changes in the counter-pressure of the cuff 101, and these cuff pressure levels are converted into an electrical signal by transducer 158 and coupled over path 106 to microprocessor 107 for processing. Also, the deflate valve 102 is connected by hose 114 via a branch connection 115 with the hose 156 leading to cuff 101. Cuff pressure levels are converted to an electrical signal by transducer 160 and coupled over path 120 to microprocessor 107 for processing. Switch 150, which is described in greater detail below, may be included to control the overall operation of the blood pressure determination.

Figure 1B:
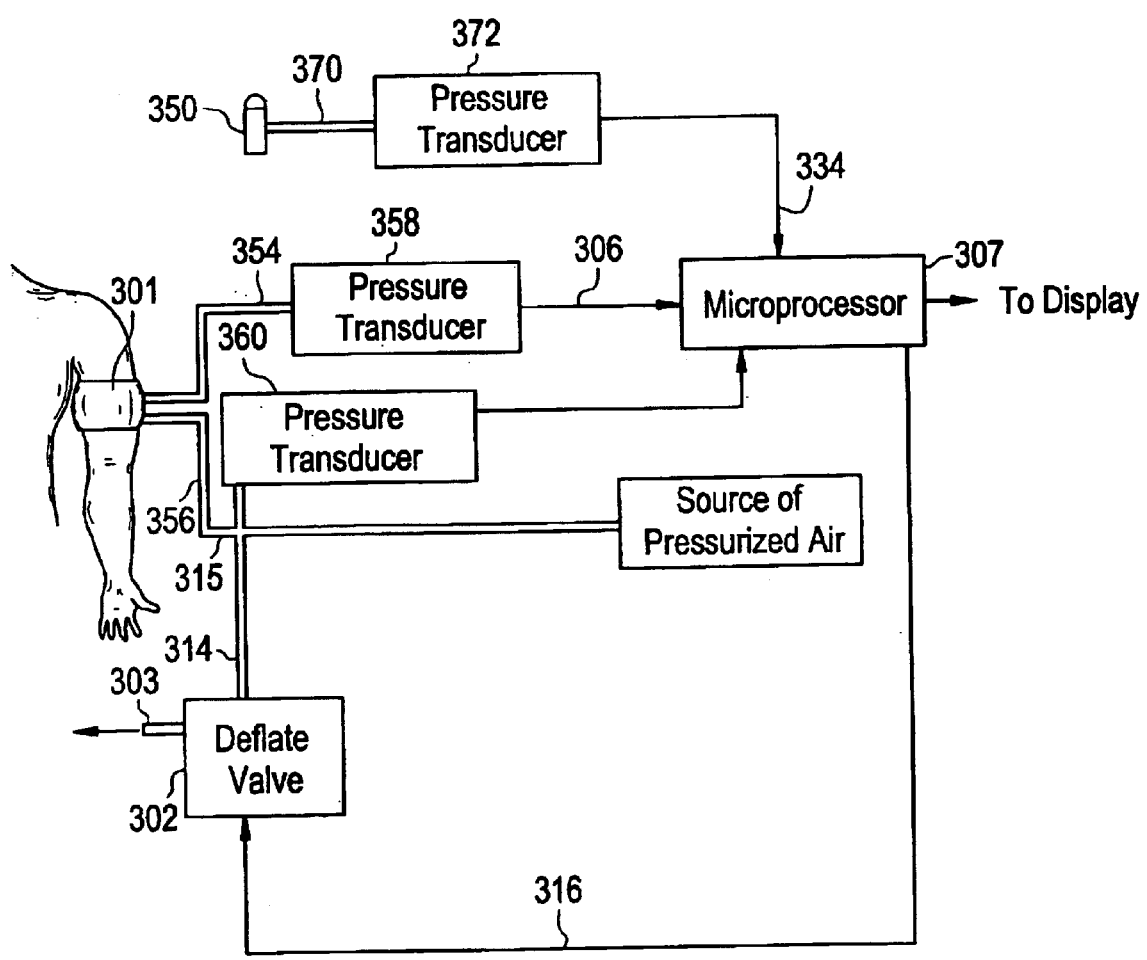
FIG. 1B is a diagram of a non-invasive blood pressure monitoring system in accordance with an embodiment of the present invention.

FIG. 1B shows the arm of a human subject wearing a flexible inflatable cuff 301 capable of occluding the brachial artery when fully inflated according to an alternative embodiment. The system of FIG. 1B is similar to the system of FIG. 1A described above except for the additional lumen 370. As such, the elements shown in FIG. 1B that correspond to like elements in FIG. 1A described above will be identified by the same reference numerals but increased by 200. As cuff 301 is deflated using deflate valve 302 having exhaust 303, the arterial occlusion is gradually relieved. The deflation of cuff 301 via deflate valve 302 is controlled by microprocessor 307 via control line 316.

A pressure transducer 358 is coupled by a hose (e.g. tube, duct, etc.) 354 to the cuff 301 for sensing the pressure therein. Cuff pressure levels in the artery are sensed by changes in the counter-pressure of the cuff 301, and these cuff pressure levels are converted into an electrical signal by transducer 358 and coupled over path 306 to microprocessor 307 for processing. Also, the deflate valve 302 is connected by hose 314 via a branch connection 315 with the hose 356 leading to cuff 301. FIG. 1B further shows hose 370 and transducer 372. Cuff pressure levels within hose 370 are converted to an electrical signal by transducer 372 and coupled over path 334 to microprocessor 307 for processing. Switch 350, which is described in greater detail below, may be included to control the overall operation of the system.

Figure 2:
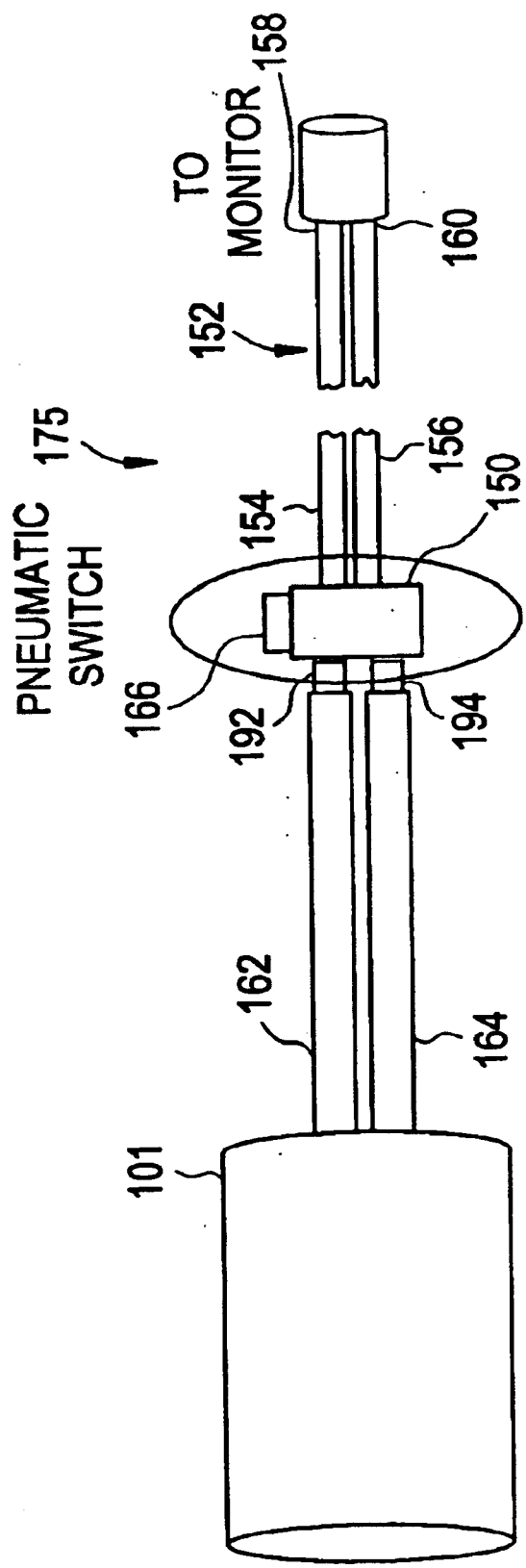
FIG. 2 is a diagram of a pneumatic non-invasive blood pressure regulating device according to an embodiment of the present invention.

FIG. 2 shows an exemplary embodiment of a pneumatic non-invasive blood pressure regulating switch 150 that may be used with the monitoring system of FIG. 1A. Referring to FIG. 2, switch 150 is shown for use with a dual-lumen hose 152 and cuff 101. Hose 152 may include a first and second lumen 154, 156. Pressure sensors 158, 160 are connected to lumens 154, 156, respectively, for sensing the pressure therein. Typically, sensors 158, 160 may exist in a monitor for displaying blood pressure data. Cuff pressure levels are converted to electrical signals for display of blood pressure (or other medical) data of a patient. Cuff 101 includes lumens 162, 164 for providing a path of pressurized air through the system. Switch 150 couples cuff 101 by way of lumens 162, 164 to lumens 154, 156. Preferably switch 150 is located near the patient end 175 of hose 152.

Switch 150 may include a button 166 (e.g., knob, switch, plunger, etc.) for controlling the overall operation of the blood pressure system. According to this embodiment, button 166 is configured so that when depressed (e.g., activated), it creates a pressure signal in one lumen greater than the pressure in the other lumen, thereby causing at least one of pressure sensors 158, 160 to measure the change in pressure. This information may then be sent to microprocessor 107. Microprocessor 107 may analyze this information in order to toggle (e.g., control, regulate, stop, restart, delay, etc.) operation of the blood pressure system. Since microprocessor 107 may be configured to identify a pressure differential between lumens 154, 156, the orientation of the system (e.g., position and attachment of hoses, lumens, sensors, cuffs, etc.) can vary. Accordingly, pneumatic switch 150 allows a caregiver to remain near a patient during a blood pressure determination and still control the overall operation of the system.

Figure 3:
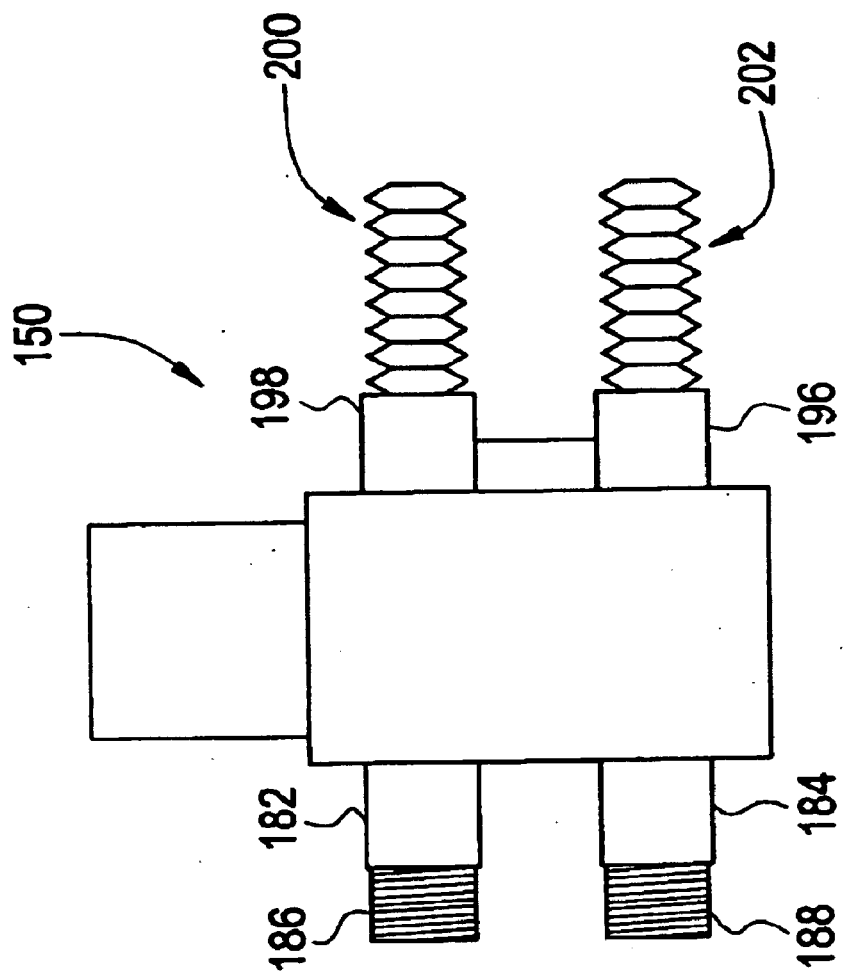
FIG. 3 is a top plan view of the pneumatic non-invasive blood pressure regulating device of FIG. 2 in greater detail.
Figure 4:
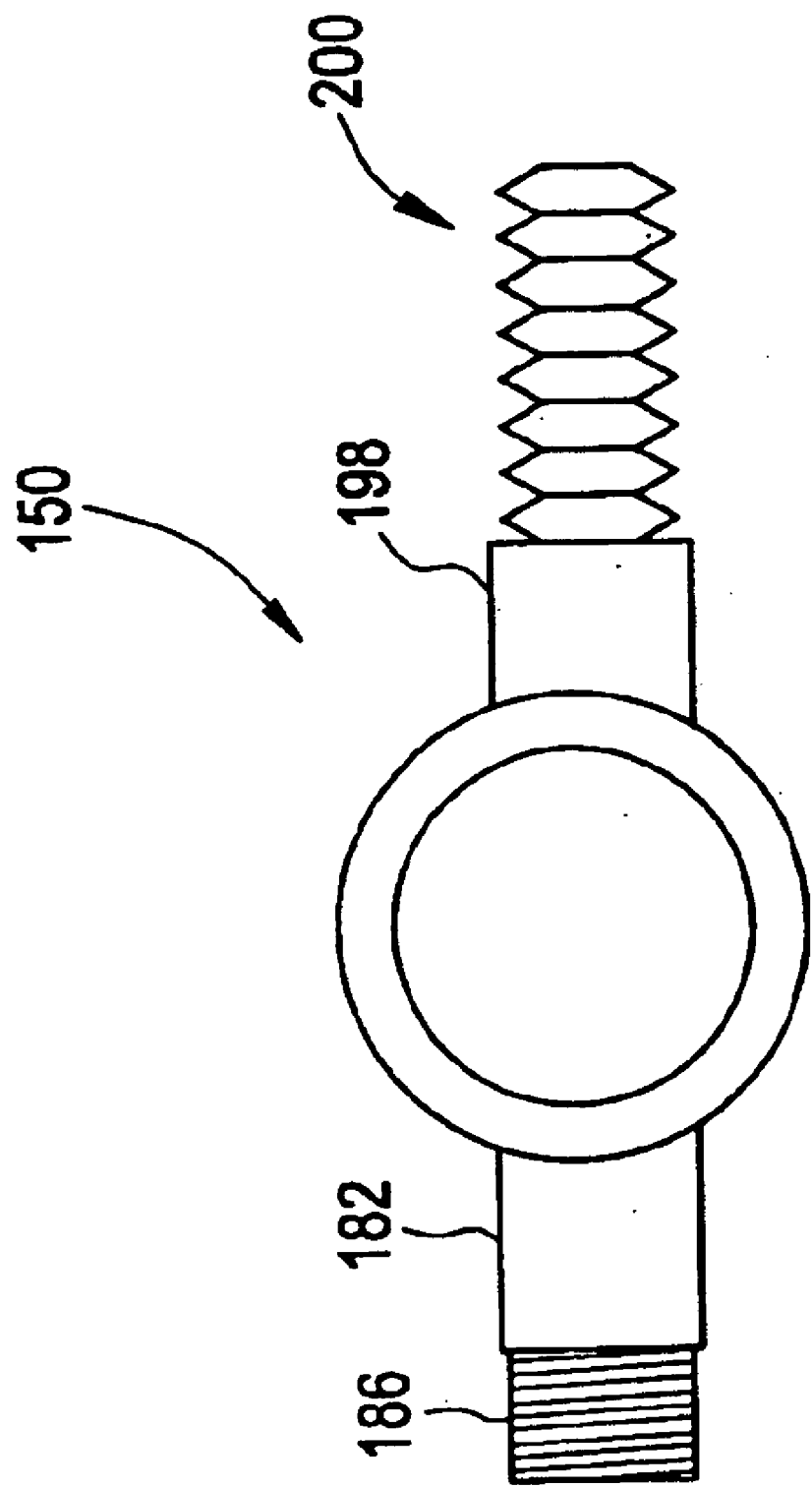
FIG. 4 is a side plan view of a pneumatic non-invasive blood pressure regulating device of FIG. 2 in greater detail.

Referring to FIGS. 3 and 4, pneumatic switch 150 is shown in greater detail. According to an exemplary embodiment, switch 150 includes cuff connectors 182, 184. Cuff connectors 182, 184 are configured to attach lumen 162, 164 to switch 150. Many different attachment methods are contemplated for connecting lumens 162, 164 to switch 150 by way of cuff connectors 182, 184. For example, FIG. 3 shows connectors 182, 184 as having externally threaded male portions 186, 188. Threaded male portions 186, 188 may be threaded into internally threaded female portions 192, 194 located on lumens 162, 164 (as shown in FIG. 2). Switch 150 further includes hose barbs 196, 198. Hose barbs 196, 198 are configured to connect switch 150 to lumens 154, 156. For example, as shown in FIGS. 3 and 4, hose barbs 196, 198 may include ridges 200, 202 for lumens 154, 156 to slide over and grip during operation. FIGS. 3 and 4 are provided as examples and are by no means intended to be limiting in any way. Thus, any number of other suitable attachment mechanisms could be used (e.g., fasteners, clamps, bolts, etc.) between switch 150 and lumens 162, 164 and barbs 196, 198.

Figure 5:
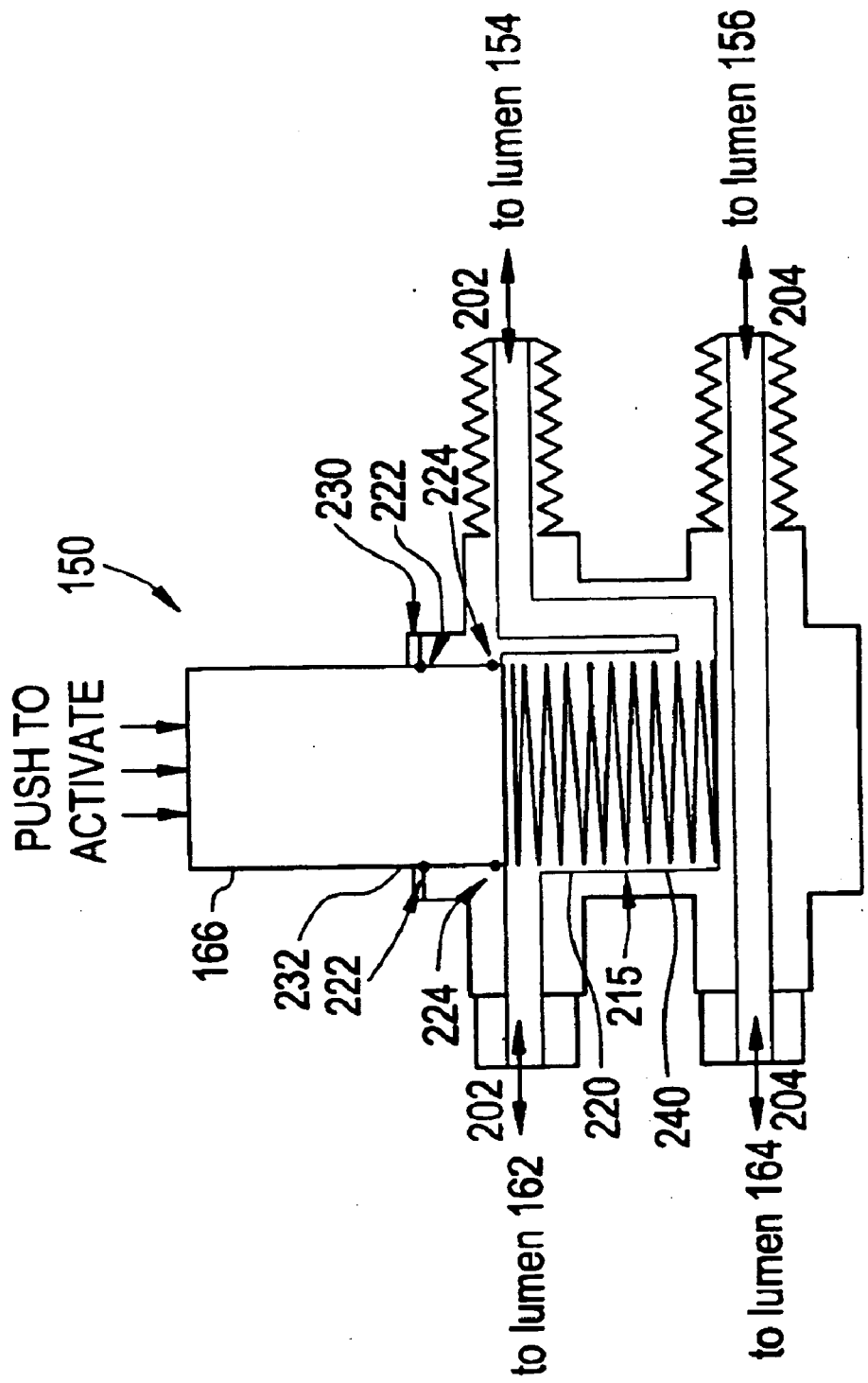
FIG. 5 is a cross-sectional view of the pneumatic non-invasive blood pressure regulating device of FIG. 2 in an extended position.
Figure 6:
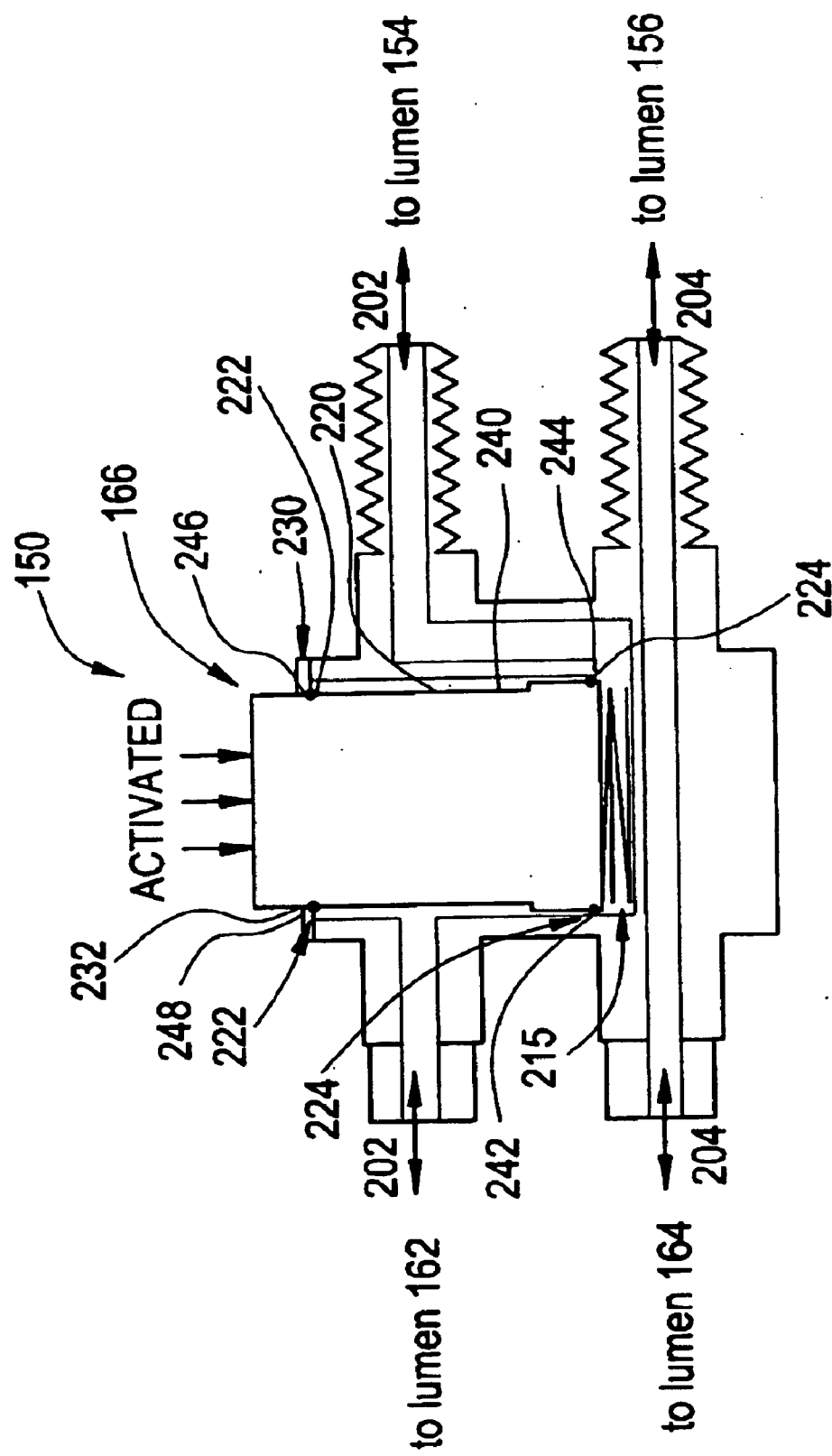
FIG. 6 is a cross-sectional view of the pneumatic non-invasive blood pressure regulating device of FIG. 2 in a compressed position.

FIGS. 5 and 6 show detailed exemplary cross-sectional views of the interior of switch 150 from FIGS. 2–4. Specifically, FIG. 5 shows switch 150 while button 166 is in an extended position and FIG. 6 shows switch 150 while button 166 is in a compressed position. As shown in FIGS. 5 and 6, pressurized air may travel through switch 150 along two separate paths. First, air may travel between lumens 154 and 162 by way of path 202. Second, air may travel between lumens 156 and 164 by way of path 204. Each path is preferably pneumatically isolated from one another. Accordingly, a pressure signal from the activation of button 166 would only exist in one path.

Referring to FIG. 5, button 166 may be configured to move between an extended position and a compressed position through an aperture 232 located on an end cap 230. Preferably, button 166 is configured to remain in an extended position when not depressed. For example, switch 150 may include a spring mechanism 215 for applying a biasing force against the bottom of button 166. Spring mechanism 215 may be positioned within a cavity 220 formed in switch 150. As spring mechanism 215 biases button 166 in an extended position, cavity 220 remains substantially unobstructed for pressurized air to flow between lumens 154, 156 and/or 162, 164 (not shown). Switch 150 further includes seals (rings) 222 and 224. These seals are preferably o-ring seals configured to create seals between button 166 and switch 150. Ring 222 may be attached to end cap 230 so that while button 166 is in the extended position, seal 222 creates a seal between button 166 and end cap 230. In addition, seal 224 may be attached to button 166 to create a seal with the upper portion of cavity 220. Each seal helps prevent pressurized air from exiting switch 150 around button 166 out through aperture 232 located on end cap 230.

Referring to FIG. 6, button 166 may be depressed (activated) to move longitudinally through cavity 220. As button 166 is activated, spring 215 is compressed thereby allowing button 166 to at least substantially fill cavity 220. Upper ring 222 provides a seal between button 166 and end cap 230 during the movement of button 166. Similarly, once button 166 moves a predetermined distance within cavity 220, lower ring 224 makes contact with a lower portion of cavity wall 240. As a result, pressurized air is blocked at points 242 and 244 by lower ring 224 and at points 246 and 248 by upper ring 222. Accordingly, a pressure signal may be created in path 202 that may be detected by sensor 158 (not shown). Based on data received from sensor 158, microprocessor 107 may thereby control operation of the system according to preprogrammed logic. Many monitors used in the art already utilize transducers that may detect the pressure signal created by switch 150.

As described above, since each of paths 202, 204 are pneumatically isolated from one another, the pressure signal in path 202 will not directly affect the flow of pressurized air along path 204. Thus, it is important to note that button 166 may be configured to work along either path. For example, even though button 166 has been described as working along path 202, it may just as easily be situated in a similar fashion with respect to path 204 to create a pressure signal therein. In addition, switch 150 may be used with a single hose system utilizing a second dedicated lumen. For example, one hose could provide the a path of pressurized air through the system and a second hose could be used as a dedicated lumen attached to the switch. Thus, the blood pressure determination data could be obtained along the path of pressurized air while the pneumatically isolated second hose and switch could control the overall operation of the system.

Figure 7:
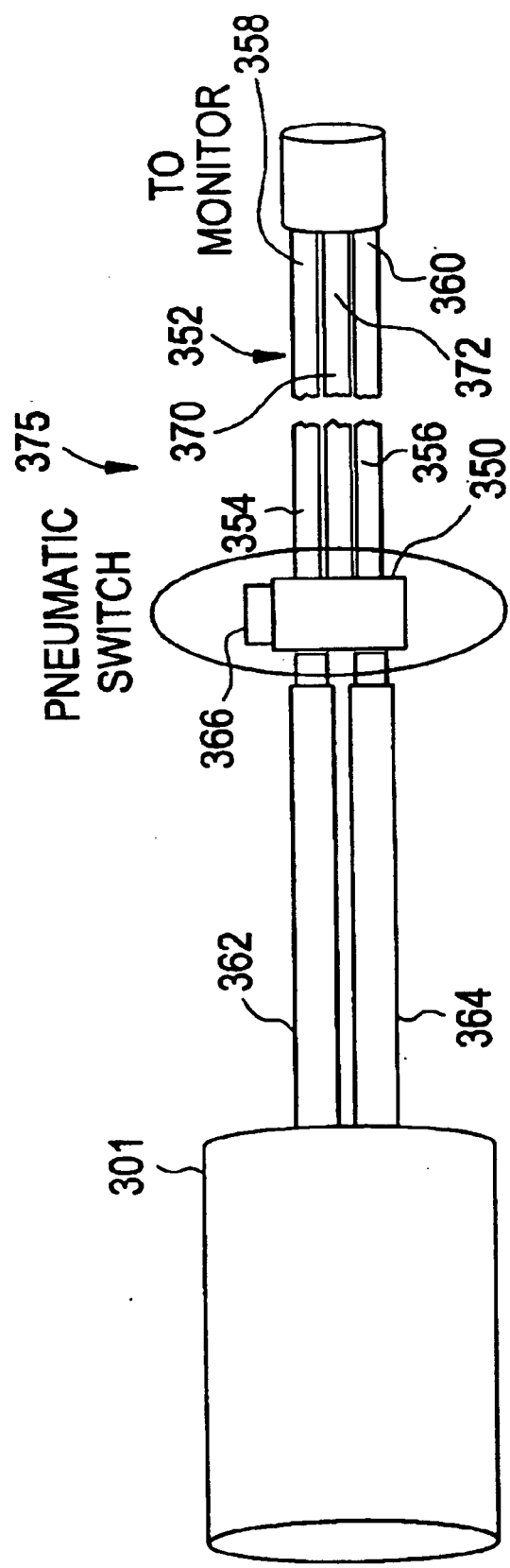
FIG. 7 is a diagram of a pneumatic non-invasive blood pressure regulating device in accordance with an alternative embodiment of the present invention.

FIG. 7 shows an alternative embodiment of a pneumatic non-invasive blood pressure regulating switch 350 that may be used with the monitoring system of FIG. 1B. For example, FIG. 7 shows switch 350 for use with a tri-lumen hose 352 and cuff 301. Hose 352 may include a first, second, and third lumen 354, 356, and 370. Although this embodiment describes a single hose 352 comprising three lumens 354, 356 and 370, alternative configurations are contemplated. For instance, lumens 354, 356 and 370 may exist outside of a single hose, may be integrally connected to one another, and/or may be detached from one another. Pressure sensors 358, 360 are connected to lumens 354, 356, respectively, for sensing the pressure therein. Typically, sensors 358, 360 may exist in a monitor for displaying blood pressure data. Cuff pressure levels are converted into electrical signals for display of blood pressure (or other medical) data of a patient. Cuff 301 includes lumens 362, 364 for providing a path of pressurized air through the system. Switch 350 couples cuff 301 by way of lumens 362, 364 to lumens 354, 356. Preferably, switch 350 is located near the patient end 375 of hose 352. It is important to note that lumen 370 preferably exists as a separate, pneumatically self-contained lumen relative to lumens 354, 356.

Switch 350 may include a button 366 (e.g., knob, switch, plunger, etc.) for controlling the overall operation of the blood pressure system. According to this embodiment, lumen 370 is configured to remain at a static pressure during normal operation of the system. However, once depressed, button 366 pneumatically creates a pressure signal in lumen 370. Pressure sensor 372 then measures the pressure signal and/or change in pressure in lumen 370. This information may then be sent to and processed by microprocessor 307 which toggles (e.g., stops, restarts, delays, etc.) operation of the blood pressure system. Since microprocessor 307 may be configured to identify a pressure change in lumen 370, the orientation of the system (e.g., position and attachment of hoses, lumens, sensors, cuffs, etc.) can vary. Accordingly, pneumatic switch 350 allows a caregiver to remain near a patient during a blood pressure determination and still control the overall operation of the system.

Figure 8:
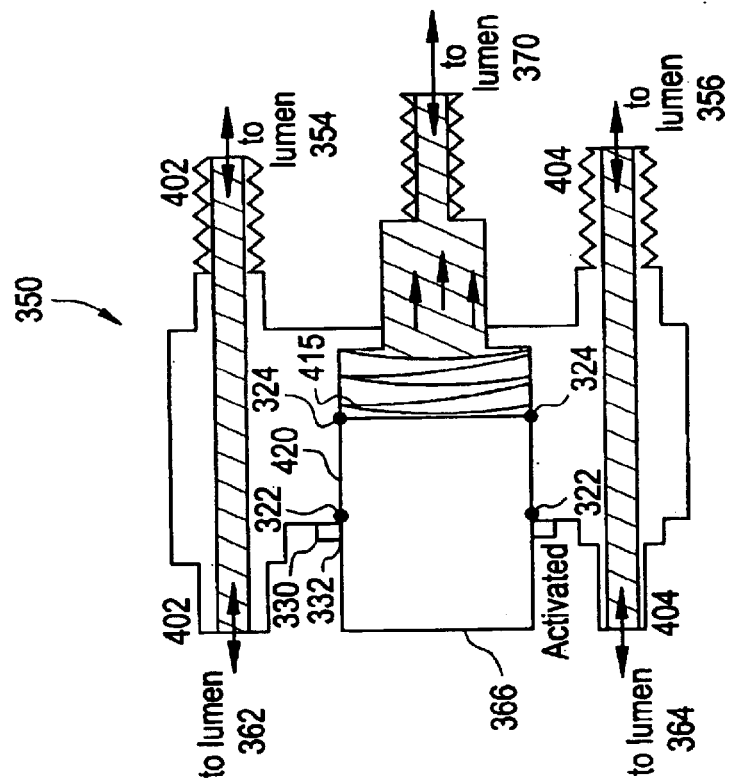
FIG. 8 is a cross-sectional view of the pneumatic non-invasive blood pressure regulating device of FIG. 7 in an extended position.
Figure 9:
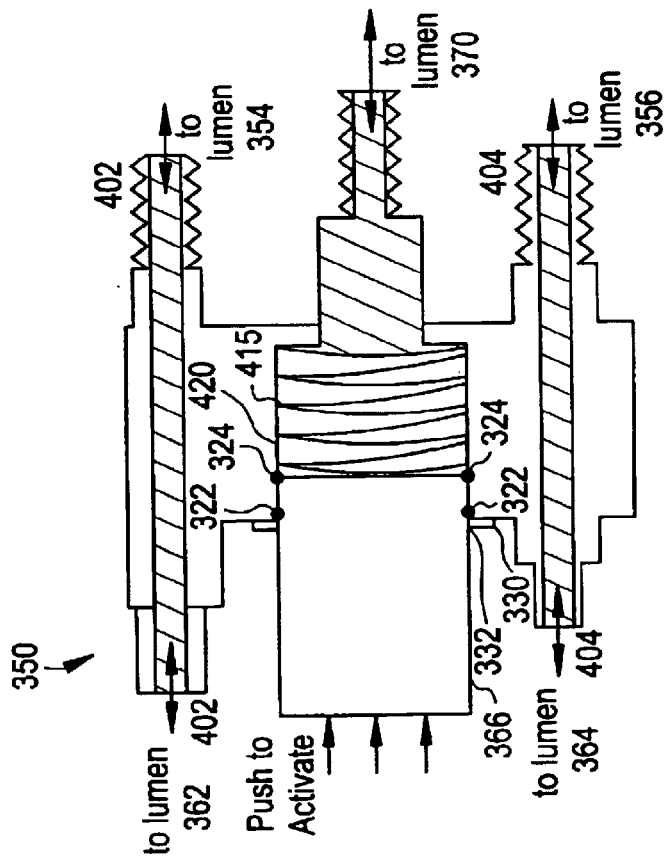
FIG. 9 is a cross-sectional view of the pneumatic non-invasive blood pressure regulating device of FIG. 7 in a compressed position.

FIGS. 8–9 show detailed exemplary cross-sectional views of the interior of switch 350 from FIG. 7. Specifically, FIG. 8 shows switch 350 while button 366 is in an extended position and FIG. 9 shows switch 350 while button 366 is in a compressed position. As shown in FIGS. 8 and 9, pressurized air may travel through switch 350 along two separate paths. First, air may travel between lumens 354 and 362 by way of path 402. Second, air may travel between lumens 356 and 364 by way of path 404. In addition, air may be held at a substantially static pressure within lumen 370. Lumen 370 is preferably pneumatically isolated from paths 402, 404 (e.g., lumen 370 exists as part of a closed system). Accordingly, a pressure signal from the activation of button 366 would only exist in lumen 370.

Referring to FIG. 8, button 366 may be configured to move between an extended position and a compressed position through an aperture 332 located on an end cap 330. Preferably, button 366 is configured to remain in an extended position when not depressed. For example, switch 350 may include a spring mechanism 415 for applying a biasing force against the bottom of button 366. Spring mechanism 415 may be positioned within a cavity 420 formed in switch 350. As spring mechanism 415 biases button 366 in an extended position, the air pressure in cavity 420 remains substantially static since lumen 370 and cavity 420 comprise a closed system. Switch 350 further includes seals (rings) 322 and 324. These seals are preferably o-ring seals configured to create seals between button 366 and switch 350. Ring 322 may be attached to end cap 330 so that while button 366 is in the extended position, seal 322 creates a seal between button 366 and end cap 330. In addition, seal 324 may be attached to button 366 to create a seal with the upper portion of cavity 420. Each seal helps prevent pressurized air from exiting switch 350 around button 366 out through aperture 332 located on end cap 330.

Referring to FIG. 9, button 366 may be depressed (activated) to move longitudinally through cavity 420. As button 366 is activated, spring 415 is compressed thereby allowing button 366 to at least substantially fill cavity 420. Upper ring 322 provides a seal between button 366 and end cap 330 during the movement of button 366. Further, lower ring 324 provides a seal between button 366 and cavity 420 during movement of button 366. Thus, as button 366 moves longitudinally through cavity 420, air in lumen 370 and cavity 420 is pressurized since lumen 370 and cavity 420 form a pneumatically isolated closed system. Accordingly, a pressure signal may be created within lumen 370 that may be detected by sensor 372 (not shown). Further, since lumen 370 is pneumatically isolated from paths 402, 404, the pressure signal will not directly affect the flow of pressurized air along either of paths 402, 404. Based on data received from sensor 372, microprocessor 307 may thereby control operation of the system according to preprogrammed logic. Many monitors used in the art already utilize transducers that may detect the pressure signal created by switch 350.

While the embodiments and application of the invention illustrated in the figures and described above are presently preferred, it should be understood that these embodiments are offered by way of example only. For example, although embodiments are described using dual and tri-lumen configurations, any number of lumens could be used (e.g., one, four, five, six, ten, etc.). In addition, the length of the hose may vary depending on the needs of the caregiver and patient. Further, the use a pneumatic controller switch is not intended to be limited to blood pressure devices or measurements. For instance, a pneumatic switch may be used in any medical situation where a caregiver desires to regulate the medical data transfer near the patient (e.g., ECG readings, blood oxygen level, body temperature, etc.). Furthermore, although the embodiments described herein relate to hand controlled switch devices, any number of variations may still be used. For example, switches controlled by a foot are also contemplated. Instead of having a switch with a button for a finger or hand to activate, a similar switch may be used that rests on the ground and may be depressed or activated by pushing it with a foot or the toes. Accordingly, the present invention is not limited to a particular embodiment, but extends to various modifications that nevertheless fall within the scope of this application.

What is claimed is:

1. An apparatus for pneumatic control of a blood pressure determination, the apparatus comprising:
   an inflatable cuff for obtaining a blood pressure measurement from a patient;
   a hose coupled to the cuff, the hose configured to operate with a pressurizing apparatus for providing pressurization of the inflatable cuff, the hose comprising a patient end and a non-patient end; and
   a pneumatic switch located in line with the hose and inflatable cuff near the patient end of the hose, the pneumatic switch being configured to control operation of the blood pressure determination.

2. The apparatus of claim 1, wherein the hose comprises a first and second lumen coupled to the pneumatic switch near the patient end of the hose.

3. The apparatus of claim 2, wherein the inflatable cuff comprises a third and fourth lumen coupled to the pneumatic switch.

4. The apparatus of claim 3, wherein the first and second lumen comprise a first and second sensor for sensing pressure therein.

5. The apparatus of claim 4, wherein the pneumatic switch includes a button configured to be depressed to create a pressure signal in the first lumen.

6. The apparatus of claim 5, wherein the first sensor senses a pressure signal and provides a signal to a microprocessor for controlling operation of the apparatus.

7. The apparatus of claim 1, wherein the hose comprises a first, second, and third lumen coupled to the pneumatic switch near the patient end of the hose.

8. The apparatus of claim 7, wherein the inflatable cuff comprises a fourth and fifth lumen coupled to the pneumatic switch.

9. The apparatus of claim 8, wherein the first, second, and third lumen comprise a first, second, and third sensor for sensing pressure therein.

10. The apparatus of claim 9, wherein the third lumen is configured to be pneumatically self-contained from the first and second lumens.

11. The apparatus of claim 9, wherein the pneumatic switch includes a button configured to be depressed to pneumatically create a pressure signal in the third lumen.

12. The apparatus of claim 11, wherein the third sensor senses a pressure signal and provides a signal to a microprocessor for controlling operation of the apparatus.

13. The apparatus of claim 1, wherein the hose comprises a lumen coupled to the pneumatic switch near the patient end of the hose.

14. The apparatus of claim 13, wherein the lumen comprises a sensor for sensing pressure therein.

15. The apparatus of claim 13, wherein the pneumatic switch is operated by using a foot.

16. The apparatus of claim 14, wherein the pneumatic switch includes a button configured to be depressed to pneumatically create a pressure signal in the lumen.

17. The apparatus of claim 16, wherein the sensor senses a pressure signal and provides a signal to a microprocessor for controlling operation of the apparatus.

18. The apparatus of claim 16 wherein the pneumatic switch further comprises at least one seal around the button to prevent air from escaping out past the button.

19. The apparatus of claim 16, wherein the button is configured to create the pressure signal within the hose when longitudinally moving from a first position to a second position.

20. The apparatus of claim 1, wherein the cuff is coupled to the hose by way of the switch.

21. The apparatus of claim 1, further comprising a display device for showing blood pressure data.

22. The apparatus of claim 1, further comprising at least one valve to regulate the pressurization of the inflatable cuff.

23. A system for pneumatically controlling a blood pressure determination, the system comprising:
    means for acquiring a blood pressure measurement from a patient;
    means for pneumatically isolating a lumen and creating a pressure signal therein;
    means for sensing the pressure signal; and
    means for providing a signal based on the pressure signal to a microprocessor in order to control overall operation of the system.

24. A method of pneumatically controlling a blood pressure determination, the method comprising:
    pressurizing an inflatable cuff of a blood pressure measurement device in order to obtain a blood pressure determination;
    creating a pressure signal in a lumen with a pneumatic switch connecting the inflatable cuff to a patient end of the lumen;
    using a sensor to sense the pressure signal; and
    signaling a microprocessor as a result of the pressure signal in order to control the blood pressure determination.

25. The method of claim 24, wherein the creating step comprises pneumatically isolating at least one lumen from a second lumen.

26. A method of pneumatically controlling a transfer of medical data, the method comprising:
    acquiring medical data from a patient using medical apparatus;
    controlling the acquisition of medical data by using a switch configured to pneumatically create a pressure change in the medical apparatus that may be sensed by a sensor; and
    signaling a microprocessor of the change, wherein the microprocessor toggles the acquisition of the medical data based on preprogrammed logic.

27. An apparatus for controlling a blood pressure determination based on a pneumatic controller switch, the apparatus comprising:
    means for acquiring a blood pressure measurement from a patient;
    means for pneumatically isolating a lumen and creating a pressure signal therein;
    means for sensing the pressure signal; and
    means for providing a signal based on the pressure signal to a computer useable medium having computer logic for enabling at least one processor in a computer system to toggle control of the blood pressure determination.

28. The apparatus of claim 27, wherein the means for acquiring medical data comprises an auscultatory technique for obtaining blood pressure.

29. The apparatus of claim 27, wherein the means for acquiring medical data comprises an oscillometric technique for obtaining blood pressure.

* * * * *